(12) United States Patent
Sakurai et al.

(10) Patent No.: US 9,417,336 B2
(45) Date of Patent: Aug. 16, 2016

(54) RADIATION IMAGE CONVERSION PANEL

(71) Applicant: HAMAMATSU PHOTONICS K.K., Hamamatsu-shi, Shizuoka (JP)

(72) Inventors: Jun Sakurai, Hamamatsu (JP); Katsuhiko Suzuki, Hamamatsu (JP); Ichinobu Shimizu, Hamamatsu (JP); Gouji Kamimura, Hamamatsu (JP)

(73) Assignee: HAMAMATSU PHOTONICS K.K., Hamamatsu-shi, Shizuoka (JP)

( * ) Notice: Subject to any disclaimer, the term of this patent is extended or adjusted under 35 U.S.C. 154(b) by 0 days.

(21) Appl. No.: 14/424,652

(22) PCT Filed: Aug. 1, 2013

(86) PCT No.: PCT/JP2013/070909
§ 371 (c)(1),
(2) Date: Feb. 27, 2015

(87) PCT Pub. No.: WO2014/034371
PCT Pub. Date: Mar. 6, 2014

(65) Prior Publication Data
US 2015/0226864 A1  Aug. 13, 2015

(30) Foreign Application Priority Data
Aug. 29, 2012  (JP) .................. 2012-188838

(51) Int. Cl.
*H05B 33/00* (2006.01)
*G01T 1/20* (2006.01)
(Continued)

(52) U.S. Cl.
CPC .................. *G01T 1/2012* (2013.01); *A61B 6/14* (2013.01); *A61B 6/4208* (2013.01); *C09K 11/7733* (2013.01); *G21K 4/00* (2013.01); *G21K 2004/06* (2013.01); *G21K 2004/10* (2013.01)

(58) Field of Classification Search
CPC ........... G21K 2004/10; G21K 2004/12; G01T 1/2012
See application file for complete search history.

(56) References Cited

U.S. PATENT DOCUMENTS 4,944,026 A * 7/1990 Arakawa ............... G01T 1/1644
250/484.4
6,744,056 B1 * 6/2004 Ogawa .................... G21K 4/00
250/484.4

(Continued)

FOREIGN PATENT DOCUMENTS

CN  102349114  2/2012
EP  1 318 525  6/2003

(Continued)

OTHER PUBLICATIONS

International Preliminary Report on Patentability dated Mar. 3, 2015 for PCT/JP2013/070909.

*Primary Examiner* — Kiho Kim
(74) *Attorney, Agent, or Firm* — Drinker Biddle & Reath LLP

(57) ABSTRACT

A radiation image converting panel includes a flexible support, a photostimulable phosphor layer provided on the main surface of the support and made of a plurality of columnar crystals, a first protective film provided on the photostimulable phosphor layer, and a second protective film provided on the first protective film, the photostimulable phosphor layer is composed of a photostimulable phosphor including Eu-doped CsBr, the first protective film is provided so as to cover the upper surface and side surface of the photostimulable phosphor layer and fill a gap of the plurality of columnar crystals in the photostimulable phosphor layer, the pencil hardness of the second protective film is not more than the pencil hardness of the first protective film, and the radiation image converting panel has a flexibility of up to a bending radius of 15 mm.

11 Claims, 13 Drawing Sheets

(51) Int. Cl.
*G21K 4/00* (2006.01)
*C09K 11/77* (2006.01)
*A61B 6/14* (2006.01)
*A61B 6/00* (2006.01)

(56) References Cited

U.S. PATENT DOCUMENTS

| | | | |
|---|---|---|---|
| 7,078,702 B2 * | 7/2006 | Ringermacher | H01L 27/14601 250/363.02 |
| 7,554,101 B2 | 6/2009 | Tahon et al. | |
| 2003/0001101 A1 * | 1/2003 | Homme | G01T 1/202 250/370.11 |
| 2003/0071228 A1 * | 4/2003 | Bergh | C09K 11/7733 250/484.4 |
| 2003/0183777 A1 * | 10/2003 | Struye | C09K 11/025 250/484.4 |
| 2004/0164251 A1 | 8/2004 | Bergh et al. | |
| 2008/0035852 A1 | 2/2008 | Nagata et al. | |
| 2008/0182109 A1 | 7/2008 | Hashimoto | |
| 2012/0025102 A1 * | 2/2012 | Yamashita | C23C 14/226 250/486.1 |

FOREIGN PATENT DOCUMENTS

| | | |
|---|---|---|
| EP | 1453066 | 9/2004 |
| JP | S62-015499 A | 1/1987 |
| JP | H6-052320 A | 2/1994 |
| JP | 2002-107495 A | 4/2002 |
| JP | 2003-139895 | 5/2003 |
| JP | 2004-340928 A | 12/2004 |
| JP | 2009-068888 A | 4/2009 |
| JP | 2011-027569 A | 2/2011 |
| JP | 2014-048059 | 3/2014 |
| WO | WO-02/23220 A1 | 3/2002 |
| WO | WO-2008/117821 A1 | 10/2008 |
| WO | WO-2012/026187 A1 | 3/2012 |

* cited by examiner (a)

|  | Through-scanner test | Bending test |
|---|---|---|
| Sample A | ○ | ○ |
| Sample B | ○ | ○ |
| Sample C | × | × |
| Sample D | × | × |

RADIATION IMAGE CONVERSION PANEL

TECHNICAL FIELD

An aspect of the present invention relates to a radiation image converting panel.

BACKGROUND ART

Conventionally, there is provided a radiation image converting panel including a photostimulable phosphor layer made of a plurality of columnar crystals. For example, Patent Document 1 discloses a phosphor panel including a support, a photostimulable phosphor layer provided on the support, a moisture-resistant protective film provided on the photostimulable phosphor layer, and a scratch-resistant protective film provided on the photostimulable phosphor layer. Also, Patent Document 2 discloses a radiation luminescence panel including a support, a photostimulable phosphor layer provided on the support, a protective film provided on the photostimulable phosphor layer, and a stain-proofing layer provided on the protective film. Also, Patent Document 3 discloses a radiation image converting panel including a phosphor layer, a protective film provided on the phosphor layer, and a damage prevention film provided on the protective film.

In the radiation image converting panels described above, the moisture resistance of the photostimulable phosphor layer is secured by the two types of protective films, while the occurrence of rupturing damage in any layer is prevented in handling of the panel or reading with a scanner device.

CITATION LIST

Patent Literature

Patent Document 1: Japanese Patent Application Laid-Open No. 2004-340928
Patent Document 2: Japanese Patent Application Laid-Open No. 2002-107495
Patent Document 3: Japanese Published Examined Patent Application No. H06-52320

SUMMARY OF INVENTION

Technical Problem

Meanwhile, when a radiation image converting panel is used as, for example, a dental imaging plate, the radiation image converting panel is inserted into the oral cavity of a patient. Because the oral cavity is three-dimensional, for acquiring detailed information as an image, it is necessary that the radiation image converting panel is bent to meet the oral shape of the patient in every shooting.

However, in the radiation image converting panel described above, the hardness of protective films has been considered in order to reduce damage, but there is no focusing on the flexibility of the radiation image converting panel. Thus, when the radiation image converting panel does not have a sufficient flexibility, the radiation image converting panel cannot be deformed to meet the oral shape of the patient, so that the setting for shooting is difficult. Also, if a radiation image converting panel not having a sufficient flexibility is bent and used, a crack may develop in the phosphor layer, or a rupture may occur in the protective film.

An aspect of the present invention has been made in view of such circumstances, and an object thereof is to provide a radiation image converting panel capable of reducing damage due to use such as reading with a scanner device and handling, and having a structure that allows use in a bent state.

Solution to Problem

An aspect of the present invention relates to a radiation image converting panel. The radiation image converting panel includes a flexible support, a photostimulable phosphor layer provided on the main surface of the support and made of a plurality of columnar crystals, a first protective film provided on the photostimulable phosphor layer, and a second protective film provided on the first protective film, the photostimulable phosphor layer is composed of a photostimulable phosphor including Eu-doped CsBr, the first protective film is provided so as to cover the upper surface and side surface of the photostimulable phosphor layer and fill a gap of the plurality of columnar crystals in the photostimulable phosphor layer, the pencil hardness of the second protective film is not more than the pencil hardness of the first protective film, and the radiation image converting panel has a flexibility of up to a bending radius of 15 mm.

This radiation image converting panel includes the flexible support, the photostimulable phosphor layer provided on the main surface of the support and made of the plurality of columnar crystals, and the first protective film provided so as to cover the upper surface and side surface of the photostimulable phosphor layer and fill a gap of the plurality of columnar crystals. The gap between the plurality of columnar crystals are thereby filled with the first protective film, which can therefore eliminate the starting point of rupturing when the radiation image converting panel is bent. Also, as a result of the plurality of columnar crystals being integrated via the first protective film, the photostimulable phosphor layer is able to follow bending of the support.

Further, the radiation image converting panel includes the second protective film provided on the first protective film. Damage due to use can thereby be reduced. Also, the pencil hardness of the second protective film is not more than the pencil hardness of the first protective film. Accordingly, the flexibility (elongation percentage) of the second protective film is not less than the flexibility (elongation percentage) of the first protective film, so that the second protective film can follow bending of the first protective film. Therefore, rupturing of the second protective film can be suppressed when the radiation image converting panel bent to a bending radius of 15 mm is used. As above, the radiation image converting panel is capable of reducing damage due to use, and enables use in a bent state.

The support may be composed of a resin film. Also, the support may be composed of polyimide. Because the support composed of a resin film such as polyimide is excellent in flexibility, the flexibility of the radiation image converting panel can be improved.

The first protective film may be a protective film with moisture resistance. As a result of the upper surface and side surface of the photostimulable phosphor layer being covered with the first protective film, moisture resistance can be improved, so that the photostimulable phosphor layer can be suppressed from absorbing moisture in the air. As a result, the photostimulable phosphor layer can be prevented from deliquescing.

The first protective film may be composed of polyparaxylylene. Because polyparaxylylene is excellent in moisture resistance, as a result of the upper surface and side surface of the photostimulable phosphor layer being covered with the first protective film composed of polyparaxylylene, moisture resistance can be improved, so that the photostimulable phosphor layer can be suppressed from absorbing moisture in the air. As a result, the photostimulable phosphor layer can be prevented from deliquescing.

The second protective film may be a protective film with scratch resistance. As a result of the second protective film being provided, damage due to use can be reduced. Also, the second protective film may be composed of a urethane-acrylic-based resin. Because a urethane-acrylic-based resin is excellent in scratch resistance and flexibility, and the pencil hardness is small, the second protective film composed of a urethane-acrylic-based resin can further reduce damage due to use, and can further improve the followability in response to bending of the first protective film. Therefore, it is made possible to further reduce damage due to use of the radiation image converting panel, and rupturing of the second protective film due to use in a bent state can be suppressed.

The radiation image converting panel may further include an excitation light absorbing layer provided on the back surface of the support that is on the side opposite to the main surface of the support. According to this arrangement, an excitation light transmitted through the photostimulable phosphor layer can be absorbed by the excitation light absorbing layer. Therefore, because an excitation light transmitted through the photostimulable phosphor layer and the support can be absorbed, a decline in contrast due to scattering and reflection of excitation light can be reduced.

The photostimulable phosphor layer may have a helical structure for which the columnar crystal is stacked in a helical shape at the side close to the support. According to this arrangement, a reflection layer is formed by the helical structure of the columnar crystal. Therefore, of the light released in the photostimulable phosphor layer as a result of the photostimulable phosphor layer being irradiated with excitation light, light guided to the side close to the support can be reflected by the helical structure, so that it becomes possible to increase the amount of light that is output from the upper surface of the photostimulable phosphor layer, without providing a reflection layer. Also, each of the plurality of columnar crystals has a helical structure. Therefore, light released in each columnar crystal is reflected by the helical structure of that columnar crystal, so that the amount of light that is output from the upper surface of the photostimulable phosphor layer can be increased, without scattering between the photostimulable phosphor layer and reflection layer.

The radiation image converting panel may further include a photostimulated luminescence reflection layer provided between the support and the photostimulable phosphor layer. According to this arrangement, of the light released in the photostimulable phosphor layer as a result of the photostimulable phosphor layer being irradiated with excitation light, light guided to the side close to the support can be reflected by the photostimulated luminescence reflection layer to increase the amount of light that is output to the side close to the upper surface of the photostimulable phosphor layer.

The first protective film may extend to over the side surface of the support. Also, the first protective film may be provided so as to cover the whole of the support and the photostimulable phosphor layer. According to this arrangement, the whole of the support and the photostimulable phosphor layer is covered with the first protective layer, so that moisture resistance can be further improved, and deliquescence of the photostimulable phosphor layer can be further prevented.

The second protective film may be provided so as to cover the first protective film. According to this arrangement, damage to the first protective film can be reduced.

The radiation image converting panel may further include a third protective film provided on the back surface of the support that is on the side opposite to the main surface of the support, and the third protective film may be a protective film with scratch resistance. According to this arrangement, damage to the back surface of the support can be reduced.

Advantageous Effects of Invention

According to an aspect of the present invention, the radiation image converting panel is capable of reducing damage due to use such as reading with a scanner device and handling, and can be used in a bent state.

BRIEF DESCRIPTION OF DRAWINGS

FIG. 3 is a chart showing test results of a through-scanner test and a bending test.

DESCRIPTION OF EMBODIMENTS

Hereinafter, embodiments of a radiation image converting panel according to an aspect of the present invention will be described in detail with reference to the drawings. Also, the same or corresponding parts will be denoted by the same reference signs in the description of the drawings, and overlapping description will be omitted.

First Embodiment

Figure 1:
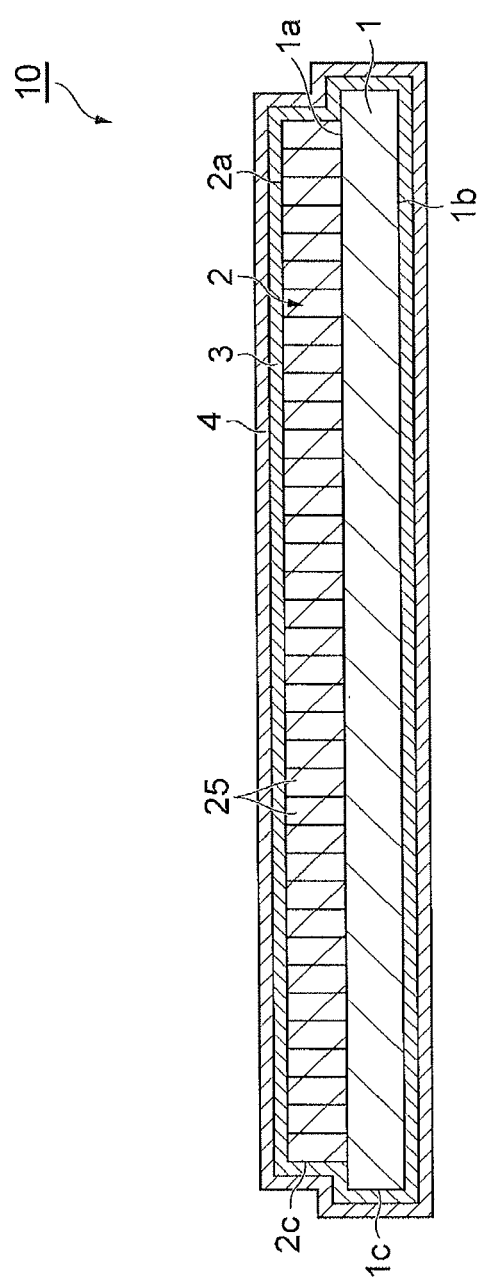
FIG. 1 is a schematic side sectional view showing a configuration of a radiation image converting panel according to a first embodiment.

FIG. 1 is a schematic side sectional view showing a configuration of a radiation image converting panel according to a first embodiment. As shown in FIG. 1, the radiation image converting panel 10 is a panel for converting incident radiation R such as X-rays into light for detection, and shows, for example, a rectangular plate shape. The length of the radiation image converting panel 10 is on the order of 100 mm, the width thereof is on the order of 100 mm, and the thickness thereof is on the order of 0.4 mm. The radiation image converting panel 10 is used as, for example, a dental imaging plate. Also, the radiation image converting panel 10 is, by combination with a HeNe laser and PMT (Photomultiplier Tube) (not shown) or the like, used as a radiation image sensor. The radiation image converting panel 10 includes a support 1, a photostimulable phosphor layer 2, a first protective film 3, and a second protective film 4.

The support 1 is a flexible base material, and shows, for example, a rectangular shape. The support 1 is composed of, for example, polyimide, PET (polyethylene terephthalate), PEEK (polyether ether ketone), PEN (polyethylene naphthalate), LCP (liquid crystal polymer), PA (polyamide), PES (polyether sulfone), PPS (polyphenylene sulfide), PBT (polybutylene terephthalate), sheet glass having a thickness of 200 μm or less, or a stainless steel foil having a thickness of 100 μm or less. The thickness of the support 1 is, for example, 10 μm or more, and is, for example, 500 μm or less. For the support 1, it suffices to have a predetermined flexibility, and a resin film is preferred.

The photostimulable phosphor layer 2 is a layer that absorbs and accumulates incident radiation. R, and releases light L according to energy of the accumulated radiation R as a result of being irradiated with excitation light. The photostimulable phosphor layer 2 is provided on a front surface 1a (main surface) of the support 1, and its thickness is, for example, 80 μm or more, and is, for example, 600 μm or less. This photostimulable phosphor layer 2 is composed of, for example, CsBr (cesium bromide) doped with Eu (europium) (hereinafter, referred to as "CsBr:Eu"), and is structured such that a plurality of columnar crystals 25 stands in a forest-like manner (referred to also as needle-like crystals). In addition, the CsBr:Eu is highly hygroscopic, and absorbs moisture in the air to deliquesce in an exposed state. Also, the wavelength range of the excitation light that is irradiated onto the photostimulable phosphor layer 2 is on the order of 550 nm to 800 nm, and the wavelength range of the light L that is released by the photostimulable phosphor layer 2 is on the order of 350 nm to 500 nm.

The first protective film 3 is a protective film with moisture resistance, and is a moisture-proofing film for suppressing the photostimulable phosphor layer 2 from absorbing moisture in the air. The first protective film 3 is provided so as to cover an upper surface 2a and side surfaces 2c of the photostimulable phosphor layer 2 and fill gaps of the plurality of columnar crystals 25 of the photostimulable phosphor layer 2. In the first embodiment, the first protective film 3 is provided so as to cover the whole of the support 1 and the photostimulable phosphor layer 2. In other words, the first protective film 3 is provided on the front surface 1a, back surface 1b, and side surfaces 1c of the support 1 as well as on the upper surface 2a and side surfaces 2c of the photostimulable phosphor layer 2, and wraps around the whole of the support 1 and the photostimulable phosphor layer 2. The thickness of the first protective film 3 is, for example, 2 μm or more, and is, for example, 20 μm or less. Also, the pencil hardness compliant with old JIS (Japanese Industrial Standards) K5400 (hereinafter, simply referred to as the "pencil hardness") of the first protective film 3 is on the order of 2H. The first protective film 3 is composed of, for example, an organic film of polyparaxylylene, polyurea, or the like or a mixture film of an organic film and an inorganic film for which a nitride film (for example, SiN, SiON), a carbide film (for example, SiC), or the like are laminated on the organic film described above. Forming an inorganic film on an organic film allows a further improvement in moisture resistance.

The second protective film 4 is a protective film with scratch resistance, and is a protective film for preventing damage that is received in handling and reading by a scanner device. The second protective film 4 is provided on the first protective film 3. In the first embodiment, the second protective film 4 is provided so as to cover the whole of the first protective film 3. In other words, the second protective film 4 is provided on the front surface 1a, back surface 1b, and side surfaces 1c of the support 1, and wraps around the whole of the support 1, the photostimulable phosphor layer 2, and the first protective film 3. The thickness of the second protective film 4 is, for example, 2 μm or more, and is, for example, 20 μm or less. Also, the pencil hardness of the second protective film 4 is equal or less than the pencil hardness of the first protective film 3, and is, for example, 2H or less. The second protective film 4 is composed of, for example, a urethane-acrylic-based resin, and is excellent in scratch resistance and flexibility. As the second protective film 4, AXEL SPICA CLEAR T by Isamu Paint Co., Ltd., SUPER DIAMOND CLEAR. Q by Kansai Paint Co., Ltd., or the like is used.

In the radiation image converting panel 10 configured as above, when radiation R (a radiation image) is made incident via the second protective film 4 and the first protective film 3, the incident radiation R is absorbed and accumulated by the photostimulable phosphor layer 2. When a red laser light or the like is thereafter irradiated as excitation light onto the photostimulable phosphor layer 2, light L according to energy of the radiation R accumulated by the photostimulable phosphor layer 2 is guided to the columnar crystals 25, and is released from the distal ends. Then, the light L released from the photostimulable phosphor layer 2 is transmitted through the first protective film 3 and the second protective film 4 in order, to be output.

Here, an example of a method for manufacturing a radiation image converting panel 10 will be described. First, on the front surface 1a of a support 1, columnar crystals 25 of CsBr:Eu are grown by a vapor-phase deposition method such as a vacuum vapor deposition method to form a photostimulable phosphor layer 2. As a result of being formed by a vapor-phase deposition method not by coating, the photostimulable phosphor layer 2 takes a structure having a plurality of columnar crystals 25. Next, a first protective film 3 is formed so as to cover the upper surface 2a and side surfaces 2c of the photostimulable phosphor layer 2 by a vapor-phase deposition method such as a CVD (Chemical Vapor Deposition) method. That is, the support 1 with the photostimulable phosphor layer 2 formed thereon is housed in a CVD apparatus to form a first protective film 3 with a thickness on the order of 10 μm. At this time, the first protective film 3 is formed by a vapor-phase deposition method not by coating, and is therefore formed also in gaps of the plurality of columnar crystals 25 of the photostimulable phosphor layer 2. Thereafter, a second protective film 4 is formed by applying, for example, a urethane-acrylic-based resin onto the first protective film 3 using a coater and curing the applied resin. In the manner as above, a radiation image converting panel 10 is fabricated.

Figure 2:
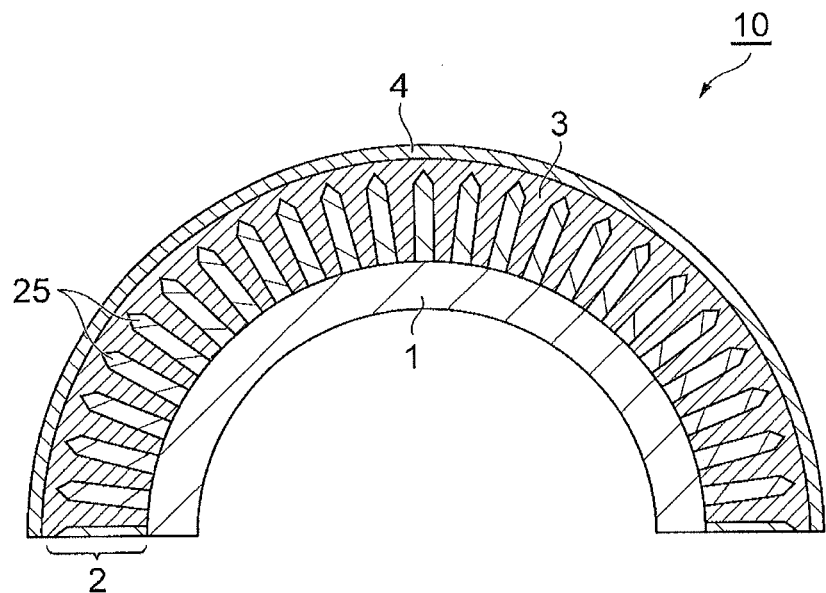
FIG. 2(a) is a view of a bent state of the radiation image converting panel of FIG. 1.
FIG. 2(b) is a view of a bent state of a radiation image converting panel of a comparative example.
Figure 2:
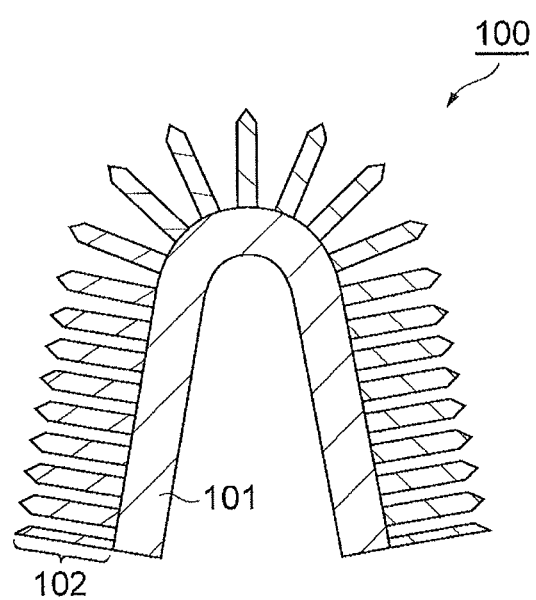

FIG. 2(a) is a view showing a bent state of the radiation image converting panel 10, and FIG. 2(b) is a view showing a bent state of a radiation image converting panel 100 of a comparative example. The radiation image converting panel 100 is a radiation image converting panel including a support 101 and a photostimulable phosphor layer 102 having a plurality of columnar crystals, and is different from the radiation image converting panel 10 in the point of not having a first protective layer and a second protective layer. The photostimulable phosphor layer 2 and the photostimulable phosphor layer 102 are both made of a plurality of columnar crystals, and have gaps between the plurality of columnar crystals.

Because the radiation image converting panel 100 does not have protective layers, the columnar crystals of the photostimulable phosphor layer 102 are opened when the radiation image converting panel 100 is bent to the back surface side of the support 101, and a crack from the gap between the plurality of columnar crystals serving as a starting point develops in the photostimulable phosphor layer 102. On the other hand, in the radiation image converting panel 10, because the first protective film 3 is provided in the gaps of the columnar crystals 25 of the photostimulable phosphor layer 2, the columnar crystals 25 are suppressed from opening even when the radiation image converting panel 10 is bent to the side of the back surface 1b of the support 1, so that the development of a crack in the photostimulable phosphor layer 2 can be suppressed.

FIG. 3 is a chart showing test results of a through-scanner test and a bending test. The through-scanner test is a test for checking if the second protective film 4 has cracked, by means of a scanner device, by passing therethrough each sample 100 times. The bending test is a test for checking if the second protective film 4 has cracked by bending and stretching each sample with a bending radius of 15 mm. "○" in the chart means that a crack in the second protective film 4 has not developed, and "×" means that a crack in the second protective film 4 has developed.

Sample A to sample D are all radiation image converting panels, and are different in only the second protective films 4. Sample A is a radiation image converting panel using a second protective film 4 (SUPER DIAMOND CLEAR Q by Kansai Paint Co., Ltd.) that is framed by thermal curing and the pencil hardness of which is HB. Sample B is a radiation image converting panel using a second protective film 4 (JUJO AP INK) that is formed by thermal curing and the pencil hardness of which is 2H. Sample C is a radiation image converting panel using a second protective film 4 (X-AHC-010 UV curable product by Idemitsu Kosan Co., Ltd.) that is formed by UV curing and the pencil hardness of which is 3H. Sample D is a radiation image converting panel using a second protective film 4 (Nittobo SSG Coat) that is formed by moisture curing and the pencil hardness of which is 7H. In addition, the supports 1 of sample A to sample D are made of polyimide, and their thickness is 125 μm. The photostimulable phosphor layers 2 of sample A to sample D are composed of CsBr:Eu, and their thickness is 180 μm. The first protective films 3 of sample A to sample D are composed of polyparaxylylene, the pencil hardness is 2H, and the thickness is 15 μm.

As shown in FIG. 3, in sample C and sample D, the second protective film 4 cracked as a result of a through-scanner test and bending test. Because flexibility is impaired when a film with a high pencil hardness is used as the second protective film 4, the possibility that the second protective film 4 ruptures thus increases.

On the other hand, in sample A and sample B, the second protective film 4 did not crack as a result of a through-scanner test and bending test. Because the pencil hardnesses of the second protective films 4 of sample A and sample B are not more than the pencil hardness of the first protective films 3, the flexibilities (elongation percentages) of the second protective films 4 are not less than the flexibility (elongation percentage) of the first protective films 3, so that the second protective films 4 can follow bending of the first protective films 3. Therefore, the second protective films 4 were suppressed from rupturing even when sample A and sample B were passed through the scanner device a plurality of times and sample A and sample B were bent and stretched with a bending radius of 15 mm.

As described above, the radiation image converting panel 10 includes the flexible support 1, the photostimulable phosphor layer 2 provided on the front surface 1a of the support 1 and made of the plurality of columnar crystals 25, and the first protective film 3 provided so as to cover the upper surface 2a and the side surfaces 2c of the photostimulable phosphor layer 2 and fill gaps of the plurality of columnar crystals 25. The gaps between the plurality of columnar crystals 25 are thereby filled with the first protective film 3, which can therefore eliminate the starting points of rupturing when the radiation image converting panel 10 is bent. Also, as a result of the plurality of columnar crystals 25 being integrated via the first protective film 3, the photostimulable phosphor layer 2 is able to follow bending of the support 1. Also, as a result of the upper surface 2a and the side surfaces 2c of the photostimulable phosphor layer 2 being covered with the first protective film 3, moisture resistance can be improved, so that the photostimulable phosphor layer 2 can be prevented from deliquescing.

Further, the radiation image converting panel 10 includes the second protective film 4 provided on the first protective film 3. Damage due to use can thereby be reduced. Also, the pencil hardness of the second protective film 4 is not more than the pencil hardness of the first protective film 3. In this case, the flexibility (elongation percentage) of the second protective film 4 is not less than the flexibility (elongation percentage) of the first protective film 3, so that the second protective film 4 can follow bending of the first protective film 3. Therefore, rupturing of the second protective film 4 can be suppressed when the radiation image converting panel 10 bent to a bending radius of 15 mm is used. When the radiation image converting panel 10 is used as, for example, a dental imaging plate, it becomes possible for the radiation image converting panel 10 to follow the shape of the inside of the oral cavity, which can facilitate the setting in shooting. As a result, it becomes possible to acquire a detailed intraoral image.

Also, because the thickness of the radiation image converting panel 10 is thin as compared with that of a radiation detector that is formed by combining an existing instantaneous light-emitting phosphor such as GOS:Tb or CsI:Tl and a CCD (Charge Coupled Device) or an FPD (Flat Panel Detector), the burden on the patient when the radiation image converting panel 10 is placed into the oral cavity and bent to be brought into contact with an object site of shooting can be reduced.

Second Embodiment

Figure 4:
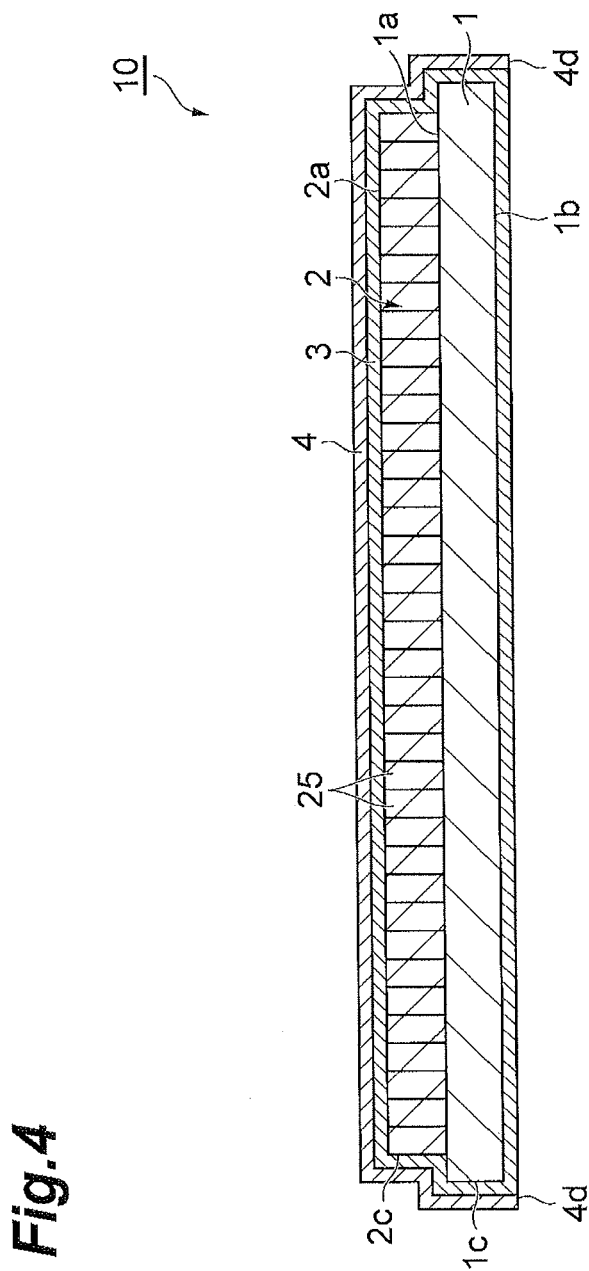
FIG. 4 is a schematic side sectional view showing a configuration of a radiation image converting panel according to a second embodiment.

FIG. 4 is a schematic side sectional view showing a configuration of a radiation image converting panel according to a second embodiment. As shown in FIG. 4, the radiation image converting panel 10 of the second embodiment is different from the radiation image converting panel 10 of the first embodiment described above in the region that the second protective film 4 covers.

In the radiation image converting panel 10 of the second embodiment, the first protective film 3 is provided on the front surface 1a, the back surface 1b, and the side surfaces 1c of the support 1 as well as on the upper surface 2a and the side surfaces 2c of the photostimulable phosphor layer 2, and wraps around the whole of the support 1 and the photostimulable phosphor layer 2. The second protective film 4 is provided on the first protective film 3 so as to cover the front surface 1a and the side surfaces 1c of the support 1, and is not provided on the back surface 1b of the support 1. In other words, the second protective film 4 has an opening 4d on the back surface 1b of the support 1.

The radiation image converting panel 10 of the above second embodiment also provides the same effects as those of the radiation image converting panel 10 of the first embodiment described above.

Third Embodiment

Figure 5:
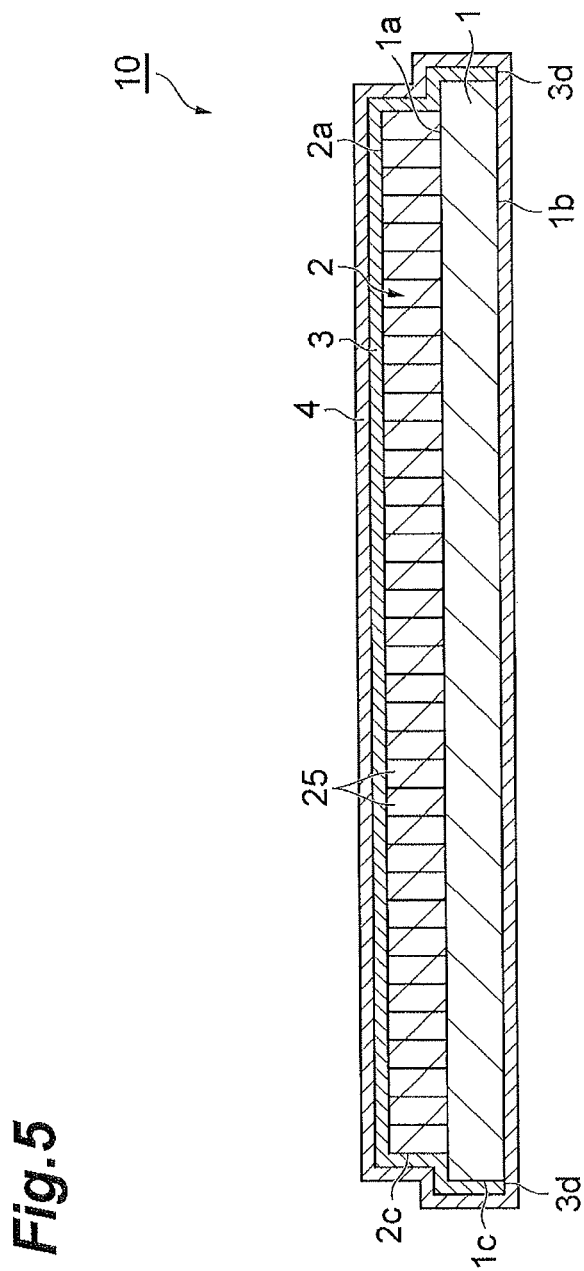
FIG. 5 is a schematic side sectional view showing a configuration of a radiation image converting panel according to a third embodiment.

FIG. 5 is a schematic side sectional view showing a configuration of a radiation image converting panel according to a third embodiment. As shown in FIG. 5, the radiation image converting panel 10 of the third embodiment is different from the radiation image converting panel 10 of the first embodiment described above in the region that the first protective film 3 covers.

In the radiation image converting panel 10 of the third embodiment, the first protective film 3 is provided on the photostimulable phosphor layer 2 so as to cover the front surface 1a and the side surfaces 1c of the support 1 as well as the upper surface 2a and the side surfaces 2c of the photostimulable phosphor layer 2, and is not provided on the back surface 1b of the support 1. In other words, the first protective film 3 has an opening 3d on the back surface 1b of the support 1. Also, the second protective film 4 is provided on the first protective film 3 so as to cover the front surface 1a, the back surface 1b, and the side surfaces 1c of the support 1, and wraps around the whole of the support 1, the photostimulable phosphor layer 2, and the first protective film 3. Also, the second protective film 4 is in contact with the back surface 1b of the support 1 via the opening 3d.

The radiation image converting panel 10 of the above third embodiment also provides the same effects as those of the radiation image converting panel 10 of the first embodiment described above.

Fourth Embodiment

Figure 6:
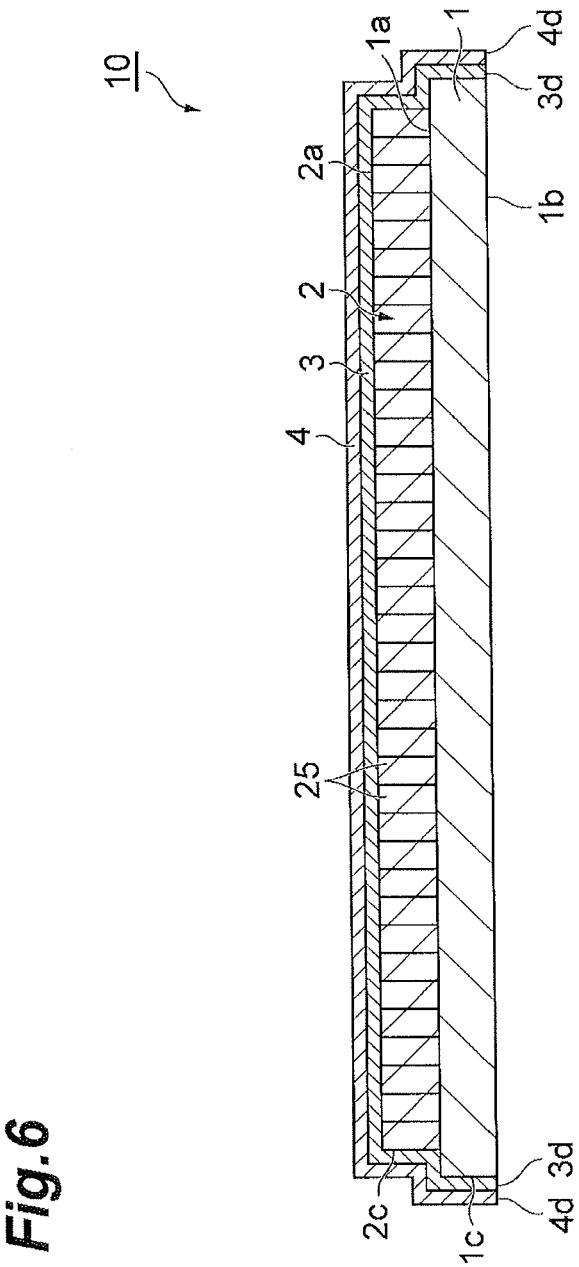
FIG. 6 is a schematic side sectional view showing a configuration of a radiation image converting panel according to a fourth embodiment.

FIG. 6 is a schematic side sectional view showing a configuration of a radiation image converting panel according to a fourth embodiment. As shown in FIG. 6, the radiation image converting panel 10 of the fourth embodiment is different from the radiation image converting panel 10 of the first embodiment described above in the region that the first protective film 3 and the second protective film 4 cover.

In the radiation image converting panel 10 of the fourth embodiment, the first protective film 3 is provided on the photostimulable phosphor layer 2 so as to cover the front surface 1a and the side surfaces 1c of the support 1 as well as the upper surface 2a and the side surfaces 2c of the photostimulable phosphor layer 2, and is not provided on the back surface 1b of the support 1. The second protective film 4 is provided on the first protective film 3 so as to cover the front surface 1a and the side surfaces 1c of the support 1, and is not provided on the back surface 1b of the support 1. In other words, the first protective film 3 has an opening 3d on the back surface 1b of the support 1, and the second protective film 4 has an opening 4d on the back surface 1b of the support 1. Therefore, the back surface 1b of the support 1 is not covered with protective films, and is exposed.

The radiation image converting panel 10 of the above fourth embodiment also provides the same effects as those of the radiation image converting panel 10 of the first embodiment described above.

Fifth Embodiment

Figure 7:
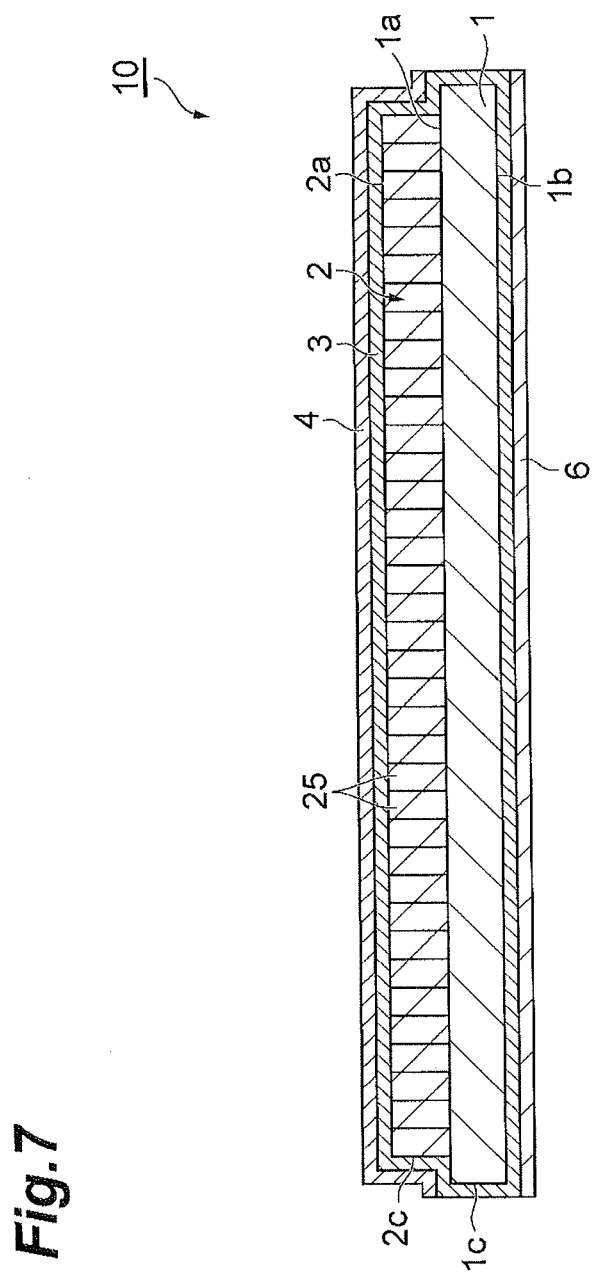
FIG. 7 is a schematic side sectional view showing a configuration of a radiation image converting panel according to a fifth embodiment.

FIG. 7 is a schematic side sectional view showing a configuration of a radiation image converting panel according to a fifth embodiment. As shown in FIG. 7, the radiation image converting panel 10 of the fifth embodiment is different from the radiation image converting panel 10 of the first embodiment described above in the region that the second protective film 4 covers and in the point of including a third protective film 6.

In the radiation image converting panel 10 of the fifth embodiment, the first protective film 3 is provided on the front surface 1a, the back surface 1b, and the side surfaces 1c of the support 1 as well as on the upper surface 2a and the side surfaces 2c of the photostimulable phosphor layer 2, and wraps around the whole of the support 1 and the photostimulable phosphor layer 2. The second protective film 4 is provided on the first protective film 3 so as to cover the front surface 1a of the support 1, and is not provided on the back surface 1b and the side surfaces 1c of the support 1. Also, the third protective film 6 is provided on the first protective film 3 so as to cover the back surface 1b of the support 1. Similar to the second protective film 4, the third protective film 6 is a protective film with scratch resistance, and is a protective film for surface protection in a reading process after irradiation with radiation R. The thickness of the third protective film 6 is, for example, 2 μm or more, and is, for example, 20 μm or less. Also, the pencil hardness of the third protective film 6 is equivalent to the pencil hardness of the second protective film 4, and is not more than the pencil hardness of the first protective film 3. The third protective film 6 may be composed of the same material as that of the second protective film 4.

The radiation image converting panel 10 of the above fifth embodiment also provides the same effects as those of the radiation image converting panel 10 of the first embodiment described above.

Sixth Embodiment

Figure 8:
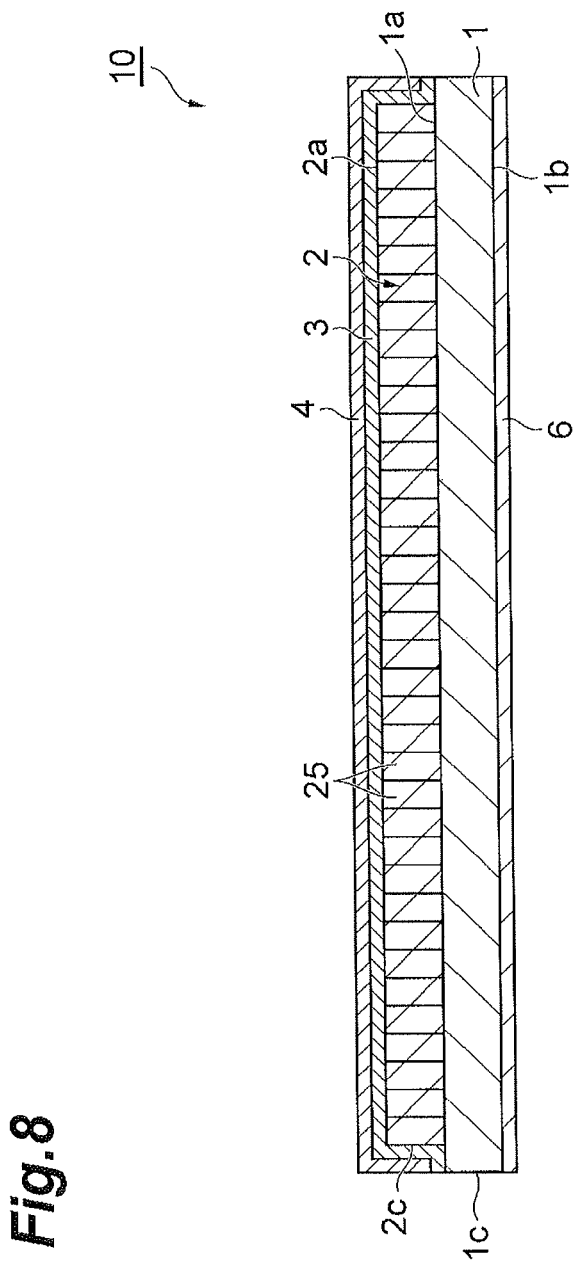
FIG. 8 is a schematic side sectional view showing a configuration of a radiation image converting panel according to a sixth embodiment.

FIG. 8 is a schematic side sectional view showing a configuration of a radiation image converting panel according to a sixth embodiment. As shown in FIG. 8, the radiation image converting panel 10 of the sixth embodiment is different from the radiation image converting panel 10 of the fifth embodiment described above in the region that the first protective film 3 covers.

In the radiation image converting panel 10 of the sixth embodiment, the first protective film 3 is provided on the front surface 1a of the support 1 as well as on the upper surface 2a and the side surfaces 2c of the photostimulable phosphor layer 2, and is not provided on the back surface 1b and the side surfaces 1c of the support 1. The second protective film 4 is provided on the first protective film 3 so as to cover the front surface 1a of the support 1, and is not provided on the back surface 1b and the side surfaces 1c of the support 1. Also, the third protective film 6 is provided on the back surface 1b so as to cover the back surface 1b of the support 1. Therefore, the side surfaces 1c of the support 1 are not covered with protective films, and are exposed.

The radiation image converting panel 10 of the above sixth embodiment also provides the same effects as those of the radiation image converting panel 10 of the first embodiment described above.

Seventh Embodiment

Figure 9:
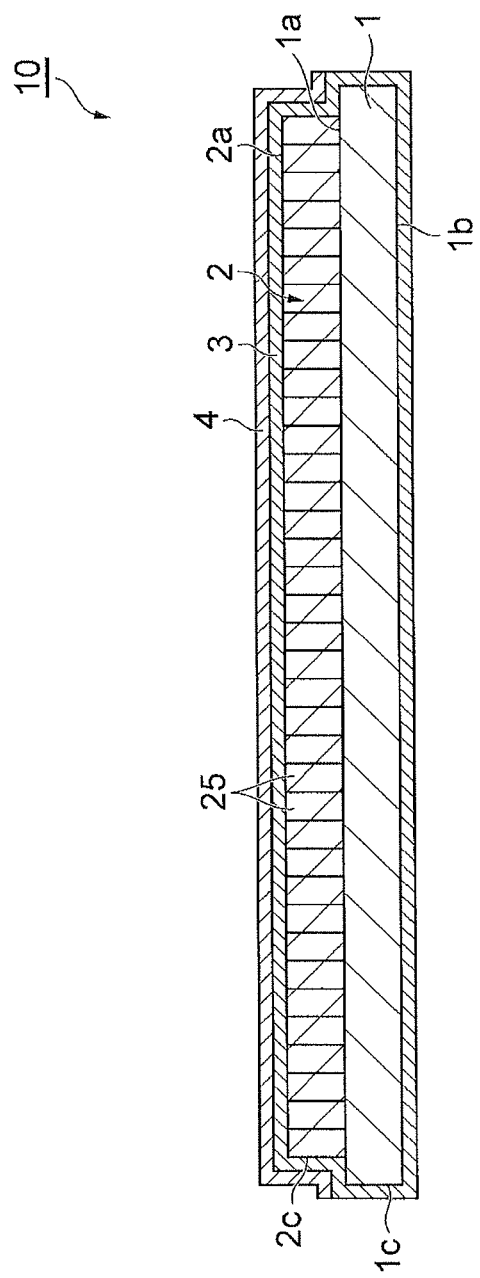
FIG. 9 is a schematic side sectional view showing a configuration of a radiation image converting panel according to a seventh embodiment.

FIG. 9 is a schematic side sectional view showing a configuration of a radiation image converting panel according to a seventh embodiment. As shown in FIG. 9, the radiation image converting panel 10 of the seventh embodiment is different from the radiation image converting panel 10 of the first embodiment described above in the region that the second protective film 4 covers.

In the radiation image converting panel 10 of the seventh embodiment, the first protective film 3 is provided on the front surface 1a, the back surface 1b, and the side surfaces 1c of the support 1 as well as on the upper surface 2a and the side surfaces 2c of the photostimulable phosphor layer 2, and wraps around the whole of the support 1 and the photostimulable phosphor layer 2. The second protective film 4 is provided on the first protective film 3 so as to cover the front surface 1a of the support 1, and is not provided on the back surface 1b and the side surfaces 1c of the support 1.

The radiation image converting panel 10 of the above seventh embodiment also provides the same effects as those of the radiation image converting panel 10 of the first embodiment described above.

Eighth Embodiment

Figure 10:
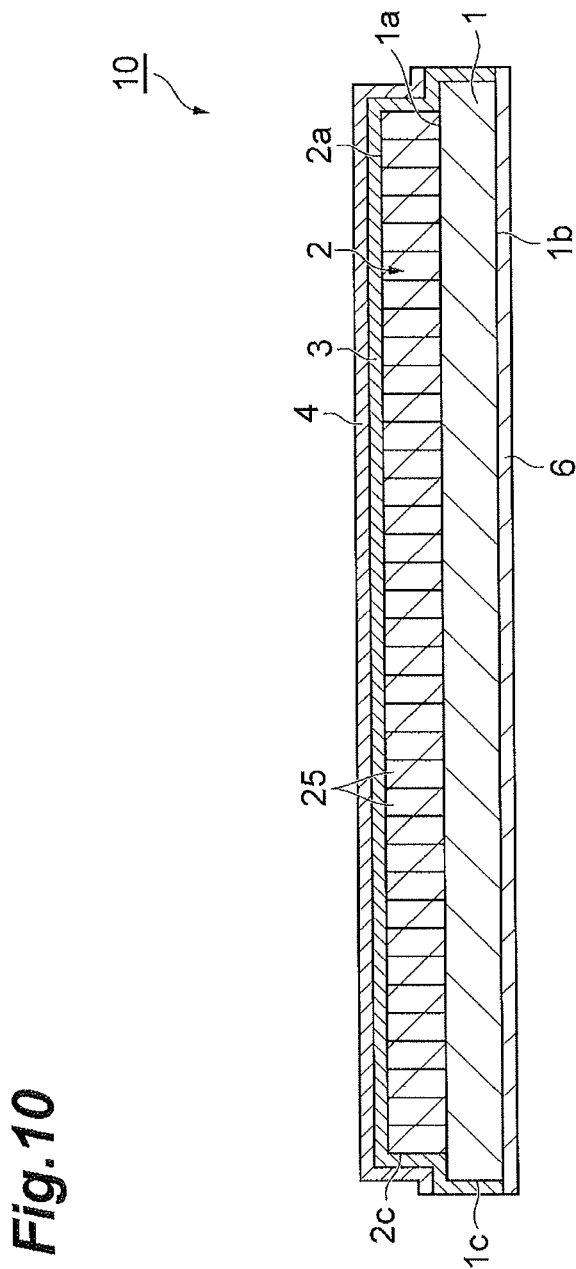
FIG. 10 is a schematic side sectional view showing a configuration of a radiation image converting panel according to an eighth embodiment.

FIG. 10 is a schematic side sectional view showing a configuration of a radiation image converting panel according to an eighth embodiment. As shown in FIG. 10, the radiation image converting panel 10 of the eighth embodiment is different from the radiation image converting panel 10 of the fifth embodiment described above in the region that the first protective film 3 covers.

In the radiation image converting panel 10 of the eighth embodiment, the first protective film 3 is provided on the photostimulable phosphor layer 2 so as to cover the front surface 1a and the side surfaces 1c of the support 1 as well as the upper surface 2a and the side surfaces 2c of the photostimulable phosphor layer 2, and is not provided on the back surface 1b of the support 1. The second protective film 4 is provided on the first protective film 3 so as to cover the front surface 1a of the support 1, and is not provided on the back surface 1b and the side surfaces 1c of the support 1. Also, the third protective film 6 is provided on the back surface 1b so as to cover the back surface 1b of the support 1. In other words, the first protective film 3 has an opening 3d on the back surface 1b of the support 1, and the third protective film 6 is in contact with the back surface 1b of the support 1 via the opening 3d.

The radiation image converting panel 10 of the above eighth embodiment also provides the same effects as those of the radiation image converting panel 10 of the first embodiment described above.

Ninth Embodiment

Figure 11:
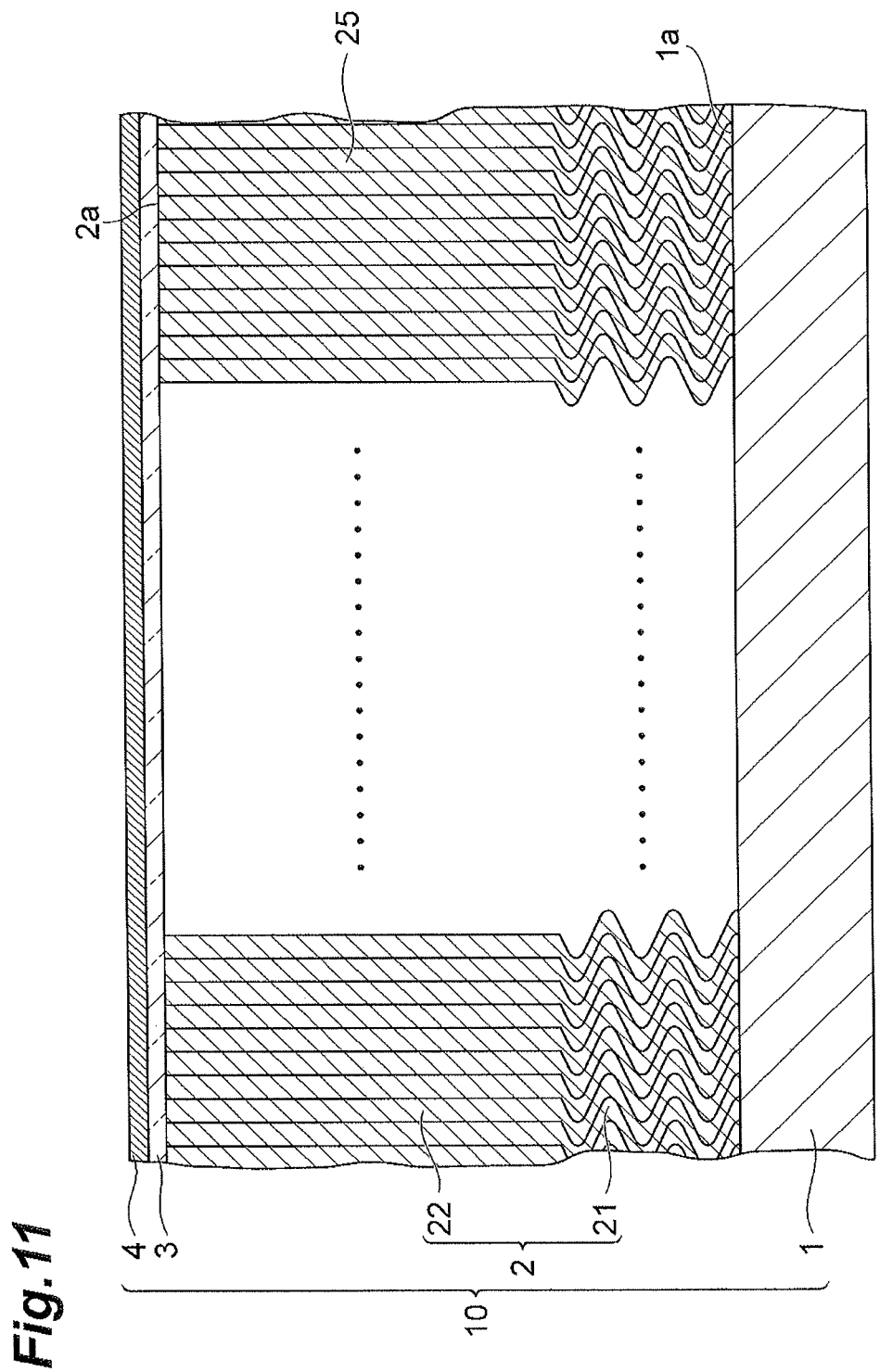
FIG. 11 is a schematic side sectional view showing a configuration of a radiation image converting panel according to a ninth embodiment.

FIG. 11 is a schematic side sectional view showing a configuration of a radiation image converting panel according to a ninth embodiment. As shown in FIG. 11, the radiation image converting panel 10 of the ninth embodiment is different from the radiation image converting panel 10 of the first embodiment described above in the configuration of the photostimulable phosphor layer 2. That is, in the radiation image converting panel 10 of the ninth embodiment, the photostimulable phosphor layer 2 is structured such that a plurality of columnar crystals 25 stands in a forest-like manner, and has a reflection layer 21 and a columnar layer 22 that are composed of the plurality of columnar crystals 25. The thickness of the photostimulable phosphor layer 2 is, for example, on the order of 50 μm to 1000 μm, and the reflection layer 21 has a thickness on the order of approximately 5 μm to the order of approximately 50 μm, which is a thickness that occupies on the order of approximately 1% to 10% of the thickness of the photostimulable phosphor layer 2.

The columnar crystals 25 are obtained by making photostimulable phosphor (CsBr:Eu) crystals grow, and their base parts at the side close to the support 1 serve as helical structure portions 23, and their parts at the side (side close to the upper surface 2a) higher than the helical structure portions 23 serve as columnar portions 24. In each columnar crystal 25, the helical structure portion 23 and the columnar portion 24 are integrally formed by continuous stacking of photostimulable phosphor crystals. In addition, the columnar crystals 25 are formed in tapered shapes in which the outer diameter of the columnar portions 24 is smaller than the outer diameter of the helical structure portions 23 and which become thicker toward the distal end side (opposite side to the support 1). Moreover, because their most distal end portions are in pointed shapes, the columnar portions 24 excluding the pointed parts are formed in tapered shapes.

Figure 12:
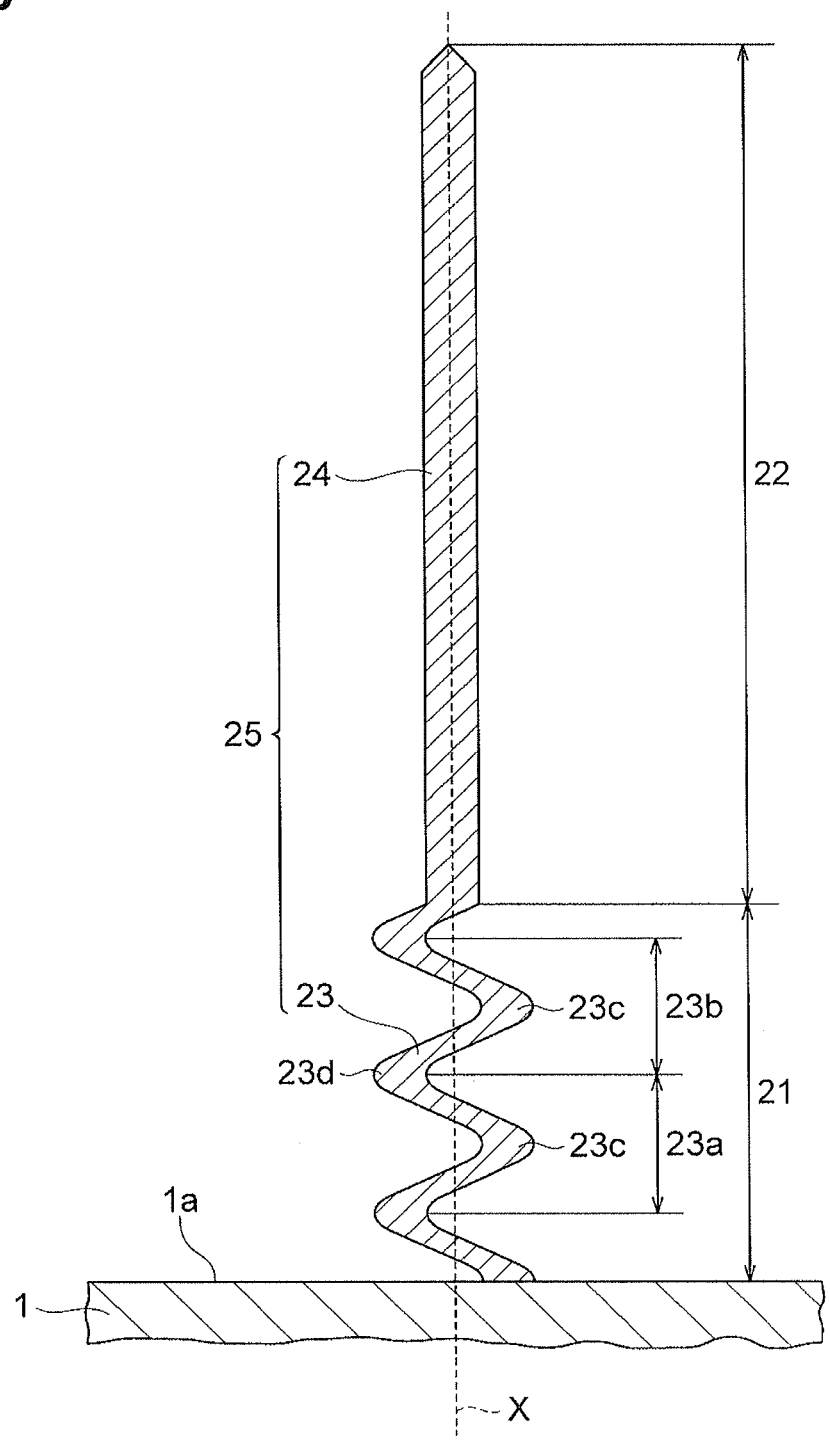
FIG. 12 is a schematic sectional view in a direction perpendicular to the support of a columnar crystal that is a component of the photostimulable phosphor layer of FIG. 11.

The helical structure portion 23 is composed of photostimulable phosphor crystals stacked into a helical shape from the front surface 1a of the support 1, and has a helical structure for which the parts (helical loops) each corresponding to one circle around a center axis X are almost regularly formed in a direction perpendicular to the front surface 1a. In FIG. 12, the range shown by reference sign 23a, 23b constitutes each one of the helical loops. The dimension of the helical loop (hereinafter, referred to also as the "helix pitch") in the direction perpendicular to the front surface 1a is on the order of approximately 0.5 μm to approximately 15 μm, and substantially the same helical loops are stacked up in plural numbers (for example, on the order of 5 to approximately 15 loops) to constitute the helical structure portion 23.

Also, the helical structure portion 23, in a section in the direction (normal axis direction) perpendicular to the front surface 1a of the support 1 as shown in FIG. 12, has a bending structure in which photostimulable phosphor crystals are almost regularly bent repeatedly to the right and left across the center axis X and which is obtained by connecting a plurality of V-shaped parts 23a and 23b with each other. The part projecting farthest to the right side in FIG. 12 of each V-shaped part 23a, 23b serves as a folding portion 23c, and the part where the V-shaped parts 23a and 23b connect with each other serves as a connecting portion 23d.

The columnar portion 24 is formed as a straight portion continuously from the helical structure portion 23, and has a columnar structure formed of photostimulable phosphor crystals extending substantially straight along a direction to intersect the front surface 1a. Moreover, the helical structure portion 23 and the columnar portion 24 are integrally formed continuously by vapor deposition.

In addition, when the columnar crystals 25, on which radiation information according to incident radiation R is accumulatively recorded, is irradiated with a red laser light or the like as excitation light, light according to the accumulated information is guided through the columnar portions 24, and is released from the distal end side (opposite side to the support 1). The reflection layer 21 reflects light that is guided to the side close to the reflection layer 21 of the light that is guided through the columnar crystal 25 to increase the amount of light that is released from the distal end side.

Figure 13:
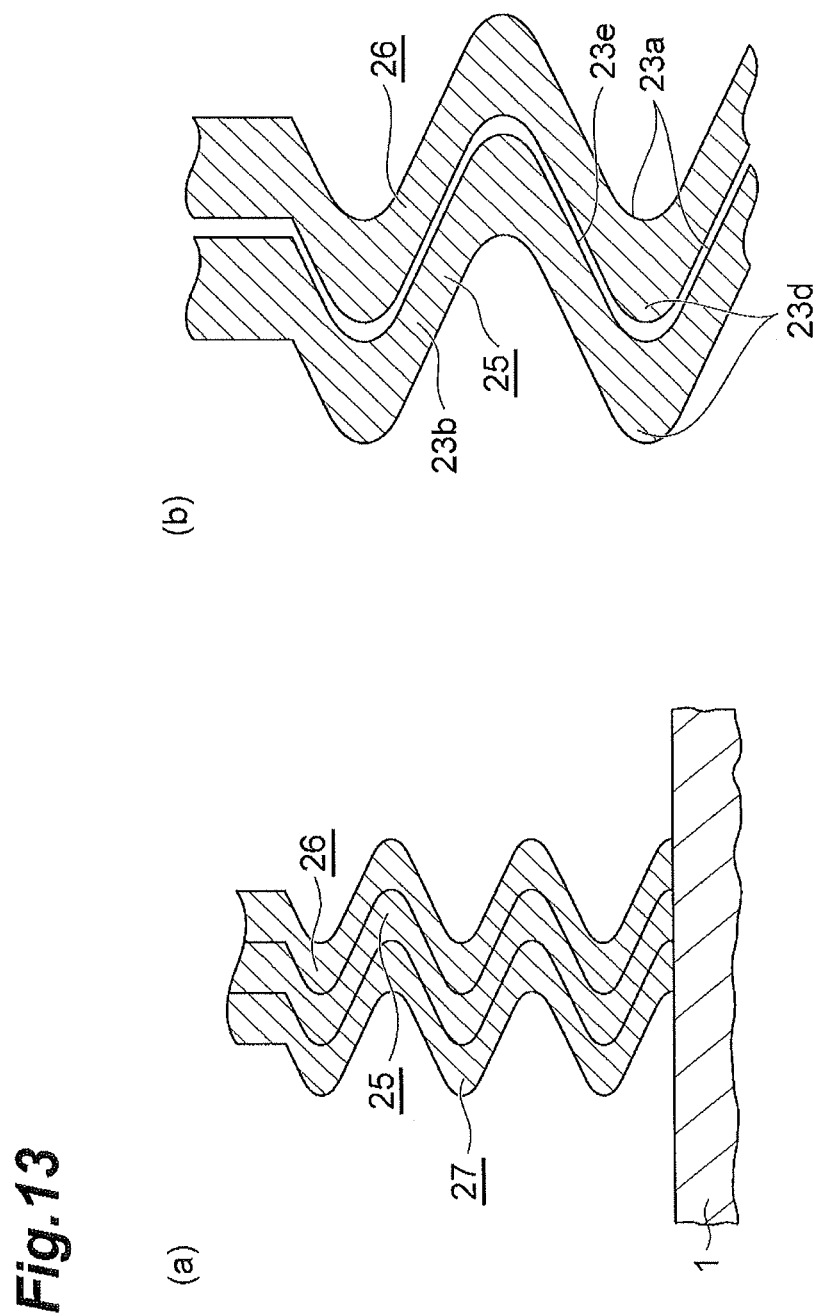
FIG. 13 are schematic sectional views in a direction perpendicular to the support of helical structure portions of the columnar crystals of FIG. 12.

Moreover, the columnar crystal 25, as shown in FIG. 13(a), in terms of the relationship with its neighboring columnar crystals 26 and 27, has a caught-in structure in which one is caught in between vertically separated parts of the other. That is, as shown in FIG. 13(b) by enlarging FIG. 13(a), the columnar crystal 25 has a caught-in structure in terms of its adjacent columnar crystal 26, 27 in which the connecting portion 23d of the columnar crystal 26 is caught in a gap 23e that is formed between the V-shaped parts 23a and 23b at the right side of the connecting portion 23d of the columnar crystal 25.

Because of this caught-in structure, a part at the side close to the columnar crystal 26 in the helical structure portion 23 of the columnar crystal 25 and a part at the side close to the columnar crystal 25 in the helical structure portion 23 of the columnar crystal 26 overlap with each other when viewed from a direction vertical to the front surface 1a of the support 1. More specifically, the folding portion 23c of the columnar crystal 25 and the connecting portion 23d of the columnar crystal 26 overlap with each other when viewed from upside. Moreover, the gap between the helical structure portion 23 of the columnar crystal 25 and the helical structure portion 23 of the columnar crystal 26 is in a wavy line shape when viewed from a direction parallel to the front surface 1a of the support 1 (the side of the side surface 1c of the support 1).

Of the columnar crystals 25 having such structures as above, the helical structure portions 23 compose the reflection layer 21, and the columnar portions 24 compose the columnar layer 22. The reflection layer 21 scatters light L by irregularly reflecting the light L when it is made incident, and therefore has a reflecting function for light L.

The radiation image converting panel 10 of the above ninth embodiment also provides the same effects as those of the radiation image converting panel 10 of the first embodiment described above. Also, the radiation image converting panel 10 of the ninth embodiment can exhibit satisfactory light reflecting characteristics even without having a light reflection film such as a metal film for enhancing reflectivity and increase the amount of light emission from the upper surface 2a, and can therefore be enhanced in the sensitivity of detecting radiation. Moreover, the radiation image converting panel 10 of the ninth embodiment is not formed with a metal film to enhance the sensitivity of detecting radiation, and is therefore provided as one that is free from the potential for corrosion caused by a metal film.

Furthermore, in the radiation image converting panel 10 of the ninth embodiment, the reflection layer 21 is composed of the helical structure portions 23 of the columnar crystals 25. As in the foregoing, because the columnar crystals 25 form a caught-in structure in which ones adjacent in the helical structure portions 23 are caught in one another, in the helical structure portions 23, the space in which no photostimulable phosphor crystals exist can be made extremely small. Therefore, because the density of photostimulable phosphor crystals in the reflection layer 21 is high, a high reflectivity is exhibited.

Moreover, as described above, applying the caught-in structure with which a slight gap is formed to the helical structure portions 23 can prevent light reflected by the helical structure portion 23 from being guided to the adjacent columnar crystal 25 to result in a decline in contrast when the helical structure portions 23 contact. Further, the helical structure portions 23 can also be increased in packing density within the panel surface to improve the reflectivity. In addition, for a higher contrast, it is desirable that all columnar crystals 25 including the helical structure portions 23 in the panel surface are separated into individual columnar crystals 25. Because the columnar crystals 25 are formed by vapor deposition, it is difficult to completely separate all columnar crystals 25, but forming the columnar crystals 25 so as to be roughly separated allows obtaining a satisfactory radiation image converting panel 10.

In addition, a radiation image converting panel according to an aspect of the present invention is not limited to those described in the above embodiments. For example, the support 1 may be a stainless steel foil, sheet glass, or the like.

Also, the radiation image converting panels 10 of the first to ninth embodiments may further include an excitation light absorbing layer provided on the back surface 1b of the support 1. When the radiation image converting panel 10 has any of the first protective film 3, the second protective film 4, and the third protective film 6, this excitation light absorbing layer may be provided between the first protective film 3, the second protective film 4, and/or the third protective film 6 and the back surface 1b of the support 1. The excitation light absorbing layer is composed of a colored resin layer made of pigment and a binder resin (besides the colored resin layer, a colored layer made of only ceramic, carbon black, chromium oxide, nickel oxide, iron oxide, or the like), and its thickness is, for example, on the order of 20 µm. A colorant to be contained in the excitation light absorbing layer is determined by the wavelength range of excitation light that is irradiated onto the photostimulable phosphor layer 2, and the light transmittance of the excitation light absorbing layer in the wavelength range of excitation light is 10% or less. In this case, because an excitation light transmitted through the photostimulable phosphor layer 2 and the support 1 can be absorbed, a decline in contrast due to scattering and reflection of excitation light can be reduced.

Also, the radiation image converting panels 10 of the first to ninth embodiments may further include a photostimulated luminescence reflection layer provided between the support 1 and the photostimulable phosphor layer 2. The photostimulated luminescence reflection layer is composed of a colored resin layer made of a white pigment and a binder resin, a metal reflection layer such as Al, a dielectric multilayer film layer made of an oxide layer such as $SiO_2$ and $TiO_2$, or the like, and its thickness is, for example, 0.001 µm or more, and is, for example, 50 µm or less. In this case, of the light released in the photostimulable phosphor layer 2 as a result of the photostimulable phosphor layer 2 being irradiated with excitation light, light guided to the side close to the support 1 can be reflected by the photostimulated luminescence reflection layer to increase the amount of light that is output to the side close to the upper surface 2a of the photostimulable phosphor layer 2.

The configuration of the columnar crystals 25 in the ninth embodiment can be applied not only to the radiation image converting panel 10 of the first embodiment, but also to the radiation image converting panels 10 of the second to eighth embodiments.

INDUSTRIAL APPLICABILITY

According to an aspect of the present invention, the radiation image converting panel is capable of reducing damage due to use such as reading with a scanner device and handling, and can be used in a bent state.

REFERENCE SIGNS LIST

1 . . . support, 1a . . . front surface (main surface), 1b . . . back surface, 1c . . . side surface, 2 . . . photostimulable phosphor layer, 2a . . . upper surface, 2c . . . side surface, 3 . . . first protective film, 4 . . . second protective film, 6 . . .

third protective film, 10 ... radiation image converting panel, 21 ... reflection layer, 23 ... helical structure portion, 25 ... columnar crystal.

The invention claimed is:

1. A radiation image converting panel comprising:
a flexible support;
a photostimulable phosphor layer provided on a main surface of the support, made of a plurality of columnar crystals;
a first protective film provided on the photostimulable phosphor layer; and
a second protective film provided on the first protective film; and the second protective film is provided along the main surface of the support, wherein
the photostimulable phosphor layer is composed of a photostimulable phosphor including Eu-doped CsBr,
the first protective film is provided in a gap of the plurality of columnar crystals in the photostimulable phosphor layer, so as to cover an upper surface and a side surface of the photostimulable phosphor layer,
a pencil hardness of the second protective film is not more than a pencil hardness of the first protective film, and
the radiation image converting panel has a flexibility of up to a bending radius of 1.5 mm,
wherein the first protective film extends to over a side surface of the support,
wherein the first protective film is provided so as to further cover the whole of the support and the photostimulable phosphor layer, and
wherein the first protective film is formed so as to suppress the columnar crystals from opening when the radiation image converting panel is bent to a side of a back surface of the support that is on a side opposite to the main surface of the support.

2. The radiation image converting panel according to claim 1, wherein the support is composed of a resin film.

3. The radiation image converting panel according to claim 1, wherein the support is composed of polyimide.

4. The radiation image converting panel according to claim 1, wherein the first protective film is a protective film with moisture resistance.

5. The radiation image converting panel according to claim 1, wherein the first protective film is composed of polyparaxylylene.

6. The radiation image converting panel according to claim 1, wherein the second protective film is a protective film with scratch resistance.

7. The radiation image converting panel according to claim 1, wherein the second protective film is composed of a urethane-acrylic-based resin.

8. The radiation image converting panel according to claim 1, further comprising an excitation light absorbing layer provided on the back surface of the support that is on a side opposite to the main surface of the support.

9. The radiation image converting panel according to claim 1, wherein the photostimulable phosphor layer has a helical structure for which the columnar crystal is stacked in a helical shape at a side close to the support.

10. The radiation image converting panel according to claim 1, further comprising a photostimulated luminescence reflection layer provided between the support and the photostimulable phosphor layer.

11. The radiation image converting panel according to claim 1, further comprising a third protective film provided on the back surface of the support that is on a side opposite to the main surface of the support, wherein
the third protective film is a protective film with scratch resistance.

* * * * *